US011020347B2

United States Patent
Buge et al.

(10) Patent No.: US 11,020,347 B2
(45) Date of Patent: Jun. 1, 2021

(54) NO-RINSE CHEMICAL FOAM CONTAINING TRIFAROTENE, AND USE THEREOF IN THE TREATMENT OF ACNE

(71) Applicant: GALDERMA RESEARCH & DEVELOPMENT, Biot (FR)

(72) Inventors: Jean-Christophe Buge, Nice (FR); Karine Nadau-Fourcade, Villeneuve Loubet (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

(21) Appl. No.: 15/763,685

(22) PCT Filed: Sep. 27, 2016

(86) PCT No.: PCT/EP2016/073009
§ 371 (c)(1),
(2) Date: Mar. 27, 2018

(87) PCT Pub. No.: WO2017/055292
PCT Pub. Date: Apr. 6, 2017

(65) Prior Publication Data
US 2018/0280297 A1 Oct. 4, 2018

(30) Foreign Application Priority Data
Sep. 29, 2015 (FR) .................................... 1559202

(51) Int. Cl.
| | |
|---|---|
| A61K 9/12 | (2006.01) |
| A61K 9/00 | (2006.01) |
| A61K 47/02 | (2006.01) |
| A61K 31/402 | (2006.01) |
| A61P 17/10 | (2006.01) |
| A61K 45/06 | (2006.01) |
| A61K 47/12 | (2006.01) |

(52) U.S. Cl.
CPC .............. *A61K 9/12* (2013.01); *A61K 9/0014* (2013.01); *A61K 31/402* (2013.01); *A61K 45/06* (2013.01); *A61K 47/02* (2013.01); *A61K 47/12* (2013.01); *A61P 17/10* (2018.01); *A61K 2300/00* (2013.01)

(58) Field of Classification Search
None
See application file for complete search history.

(56) References Cited

U.S. PATENT DOCUMENTS

| | | | |
|---|---|---|---|
| 5,952,372 A | 9/1999 | McDaniel | |
| 6,133,310 A | 10/2000 | Parks | |
| 6,177,092 B1 * | 1/2001 | Lentini | A61K 8/046 424/401 |
| 6,649,186 B1 | 11/2003 | Robinson et al. | |
| 2002/0061855 A1 | 5/2002 | Parks | |
| 2004/0184992 A1 | 9/2004 | Abram | |
| 2005/0123487 A1 | 6/2005 | Spadini et al. | |
| 2007/0237724 A1 | 10/2007 | Abram et al. | |
| 2009/0191248 A1 | 7/2009 | Hoffman et al. | |
| 2009/0214628 A1 | 8/2009 | De Rijk et al. | |
| 2010/0291160 A1 | 11/2010 | Carver et al. | |
| 2011/0008267 A1 | 1/2011 | Arkin et al. | |
| 2011/0236503 A1 | 9/2011 | Kalli | |
| 2011/0311592 A1 | 12/2011 | Birbara | |
| 2012/0114574 A1 | 5/2012 | Touitou | |
| 2013/0244976 A1 | 9/2013 | Inamoto et al. | |
| 2013/0317108 A1 | 11/2013 | At | |
| 2013/0338230 A1 | 12/2013 | At | |
| 2013/0338235 A1 | 12/2013 | At | |
| 2014/0364504 A1 | 12/2014 | Uddin | |
| 2015/0306124 A1 | 10/2015 | Manetta et al. | |
| 2017/0172877 A1 | 6/2017 | Buge et al. | |
| 2017/0172972 A1 | 6/2017 | Buge et al. | |
| 2018/0064638 A1 | 3/2018 | Tamarkin et al. | |

FOREIGN PATENT DOCUMENTS

| | | |
|---|---|---|
| CN | 104382863 A | 3/2015 |
| DE | 10 2008 029 357 A1 | 12/2009 |
| EP | 1 043 023 A1 | 10/2000 |
| FR | 2761600 A1 | 10/1998 |
| FR | 2924944 A1 | 6/2009 |
| FR | 2943914 A1 | 10/2010 |
| JP | 2002-529391 A | 9/2002 |
| JP | 2004-217675 A | 8/2004 |
| WO | WO-00/27356 A1 | 5/2000 |
| WO | WO-03/030664 A1 | 4/2003 |
| WO | 2004/037225 A2 | 5/2004 |
| WO | WO-2005/058272 A1 | 6/2005 |

(Continued)

OTHER PUBLICATIONS

International Search Report and English translation dated Nov. 29, 2016 corresponding to International Patent Application No. PCT/EP2016/073009, 5 pages.

(Continued)

*Primary Examiner* — Robert A Wax
*Assistant Examiner* — Randeep Singh
(74) *Attorney, Agent, or Firm* — Foley & Lardner LLP; Sunit Talapatra

(57) ABSTRACT

A self-foaming composition is described that includes trifarotene, for a no-rinse topical application and for application to the skin. The composition can include: at least one intermediate composition B including a gas-generating agent; at least one intermediate composition A including an agent for activating the gas-generating agent; and trifarotene or one of the pharmaceutically acceptable salts thereof being present in at least one of the intermediate compositions A and B. The composition is particularly intended for the treatment of acne. Also described is a kit or a single container including a plurality of compartments including such a composition.

28 Claims, 3 Drawing Sheets

(56) References Cited

FOREIGN PATENT DOCUMENTS

Figure 1:
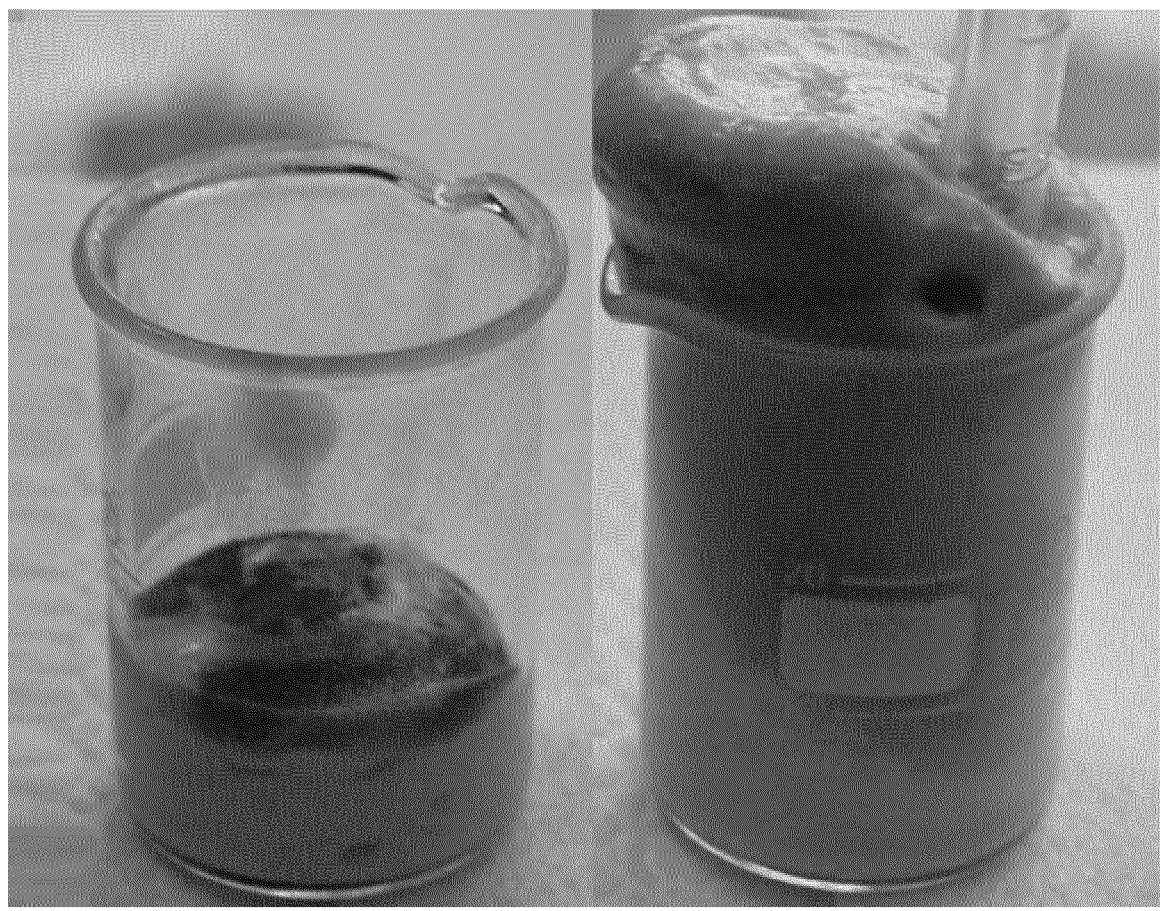

| WO | WO-2009/069006 A2 | 6/2009 |
| --- | --- | --- |
| WO | WO-2012/001065 A2 | 1/2012 |
| WO | WO-2012/085480 A1 | 6/2012 |
| WO | WO-2012/085481 A1 | 6/2012 |
| WO | WO-2012/085483 A1 | 6/2012 |
| WO | WO-2014/201541 A1 | 12/2014 |
| WO | 2015/082659 A1 | 6/2015 |

OTHER PUBLICATIONS

Written Opinion of the International Searching Authority dated Nov. 29, 2016 corresponding to International Patent Application No. PCT/EP2016/073009, 5 pages.

Wikimedia Commons; "Citric Acid Speciation" https://commons.wikimedia.org/wiki/File:Citric_acid_speciation.png; accessed Jan. 10, 2020 (Year: 2011).

Onset Therapeutics, LLC, "Benzefoam Ultra", Drug Information Online—Drugs.com, Apr. 3, 2011, XP002739766. 9 pages.

\* cited by examiner

NO-RINSE CHEMICAL FOAM CONTAINING TRIFAROTENE, AND USE THEREOF IN THE TREATMENT OF ACNE

CROSS-REFERENCE TO PRIOR APPLICATIONS

This application is a National Stage of PCT/EP2016/073009, filed Sep. 27, 2016, and designating the United States (published on Apr. 6, 2017, as WO 2017/055292 A1), which claims priority under 35 U.S.C. § 119 to French Application No. 1559202, filed Sep. 29, 2015, each hereby expressly incorporated by reference in its entirety and each assigned to the assignee hereof.

The present invention relates to a leave-on topical product in the form of a foam for the pharmaceutical or cosmetic treatment of the skin, comprising trifarotene. Trifarotene is a novel retinoid and corresponds to 3"-tert-butyl-4'-(2-hydroxyethoxy)-4"-pyrrolidin-1-yl[1,1':3',1"]terphenyl-4-carboxylic acid, of the same pharmacological class as tazarotene (arotenoids).

The present invention also relates to the use of the product according to the invention for treating acne.

Despite all the progress made, consumers are still in search of compositions intended for topical application that are more practical and rapid. Foams make it possible to overcome the problems of tolerance by better control of the dose, by virtue of their spreading properties and their low density.

In addition, some compounds used in compositions intended for a known topical application may result in side-effects that may limit the use and thus the effectiveness thereof. For example, some active principles have the major drawback of inducing irritation which may result in mediocre tolerance of the product. This may thus create, on the part of the patient, behavior of non-compliance with the treatment and of dissatisfaction regarding said treatment.

There is thus a need to develop novel galenical forms that overcome the drawbacks mentioned previously in terms of tolerance, efficacy and compliance.

Furthermore, trifarotene, like many retinoids, is known to be poorly tolerated by consumers who are following a treatment for acne. This tolerance is very variable as a function of the formulation serving as vehicle therefor. The patient also often has the impression that by applying larger amounts of product, he will be cured faster. This behavior leads to excessive irritation, non-compliance with the dosage and stoppage of the treatment.

There is also a need for novel galenical forms and in particular of foam or foaming composition type which allow better control of the dose and in which trifarotene is stable, well-tolerated, effective and pleasant to apply.

The composition according to the invention has the advantage of being in the form of a foam which is generated at the time of use, and which is very well tolerated.

After its application, the composition according to the invention is not removed by rinsing.

One of the advantages of the composition of the invention is that it is particularly well tolerated, despite the fact that it is not removed by rinsing, as is shown by the examples illustrating one of the methods of evaluating the tolerance which are presented below.

Various methods exist for evaluating the tolerance of a pharmaceutical or cosmetic product for cutaneous use, among which may be mentioned the in vivo "in used" or "human patch test" test but also the in vitro test, such as the test for measurement of the irritation on Reconstructed Human Epidermis (RHE) described in the OECD TG 439 protocol. The latter method is described in detail in example 3.

Furthermore, the present invention also has the advantage of remaining on the surface of the skin (essentially stratum corneum and epidermis) so as to avoid adverse effects such as irritation and to obtain a foam that is suitable for treating acne.

The efficacy of an active principle is associated with the release and the penetration kinetics of the active agent through the skin. The formulary composition plays its fundamental role as a vehicle for the active principle so that said active principle can reach its therapeutic target. The release-permeation test described in example 5 on ex-vivo human skin highlights the advantage of applying a chemical foam containing trifarotene.

Thus, the formulations of the invention make it possible to obtain a foam composition which can reduce the adverse effects and especially irritation.

Foams or foaming compositions currently exist on the market. However, they all have a certain number of drawbacks:

This is because three types of foams or foaming compositions exist:

Aerosols, in which the foam is generated by a propellant gas but with the drawback of being aerosols having the well-known risks of the latter (contamination and breathing risks in particular).

Expanded creams, in which air bubbles are introduced into the product via a particular manufacturing process. This process has the drawback of being restricting at the industrial level and requires major capital expenditure with regard to the packaging equipment.

Foaming formulations which are low in foaming surfactants but packaged a packaging equipped with a mechanical foam-generating system (pump with grille of Pulvorex type). This type of formulation requires the use of foaming surfactants, which may lead to irritation in the case of leave-on products.

Thus, the need therefore remains to develop a pharmaceutical composition, the galenical form of which is different from the known galenical forms, in order, inter alia, to provide compositions intended for topical application containing trifarotene in well-tolerated compositions intended for topical application to human beings, in particular leave-on compositions (i.e. the composition is not removed by rinsing after it has been applied).

The aim of the present invention is thus to provide a composition which meets these needs.

The Applicant has thus developed a novel pharmaceutical composition intended for a leave-on topical application, which is in the form of a foam which advantageously does not contain any foaming surfactant. The term "foaming surfactant" defines surfactants which produce a voluminous, stable and creamy foam when they are mixed with water according to tests that are well known to those skilled in the art.

The following constitute foaming surfactants: anionic surfactants, cationic surfactants, amphoteric surfactants and nonionic surfactants of the family of alkylpolyglucosides and glucamides.

The galenical form according to the invention has the advantage of ensuring good stability of trifarotene. Furthermore, this formulation advantageously results in the production of a mild foam which is fully tolerated and non-irritant, which allows better coverage of the area to be treated and which makes it possible to overcome the problems of tolerance by better control of the dose, by virtue of the spreading properties and the low density of the foam.

Finally, advantageously, this galenical form does not require, for the implementation thereof, the use of propellant gases or aerosols. Thus, "aerosol" or "spray" foams are excluded from the scope of the invention. Likewise, the foams of the prior art of expanded cream and/or foaming formulation type requiring a mechanical foam-generating system (Pulvorex type) are also excluded from the invention.

Finally, a subject of the present invention is the cosmetic use of the composition according to the invention, by topical application of this composition to the skin, and also a medicament intended for topical application to the skin, comprising such a composition.

A subject of the present invention is also the composition according to the invention, for its use in the treatment of acne.

The present invention will be described in greater detail in the description and the examples hereinbelow and in the light of the figures appended to the present application.

FIG. 1 illustrates the production of a composition in foam form in accordance with the invention. The left-hand photograph represents the moment of mixing (TO) and the right-hand photograph represents the foam obtained when the acid/base chemical reaction is complete.

Figure 2:
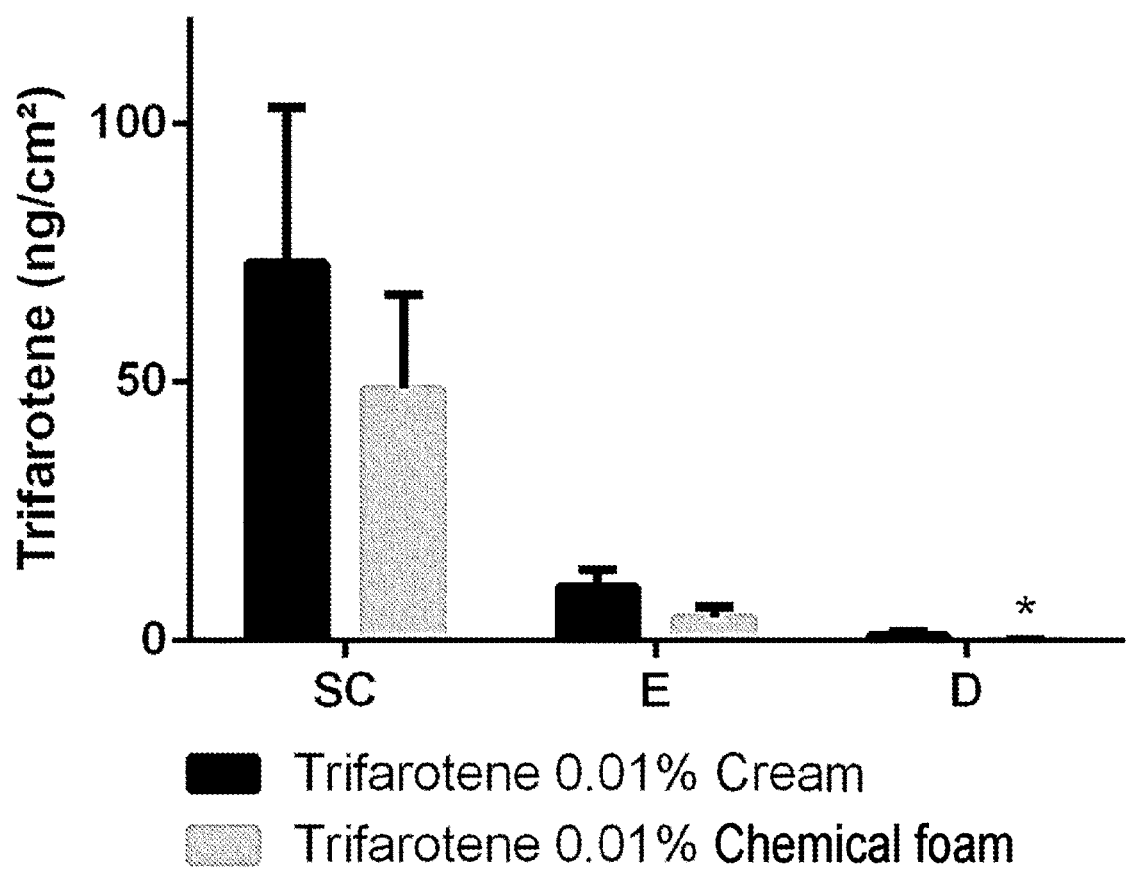

FIG. 2 illustrates example 5 and represents the comparative results of penetration-permeation into the stratum corneum, the epidermis and the dermis of a foam composition according to the invention containing 0.01% by weight of trifarotene composed of the mixture of intermediate compositions A2 and B3 described in example 1 (in a 50/50 weight ratio) and of a Reference in cream form containing 0.01% by weight of trifarotene.

Figure 3:
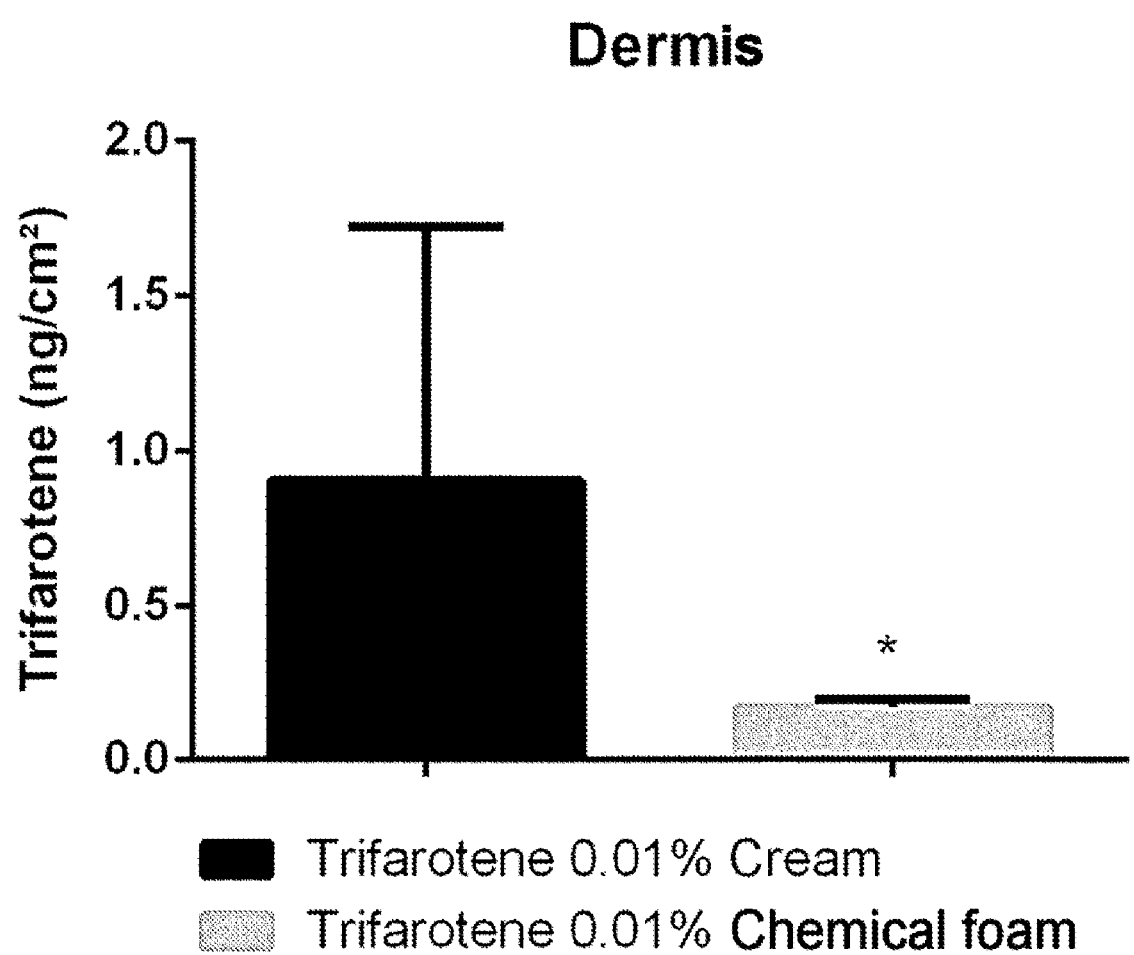

FIG. 3 also illustrates example 5 and represents the comparative results of penetration-permeation into the dermis of FIG. 1 on an enlarged scale.

The composition according to the invention is capable of taking the form of a foam solely by virtue of its composition, and may also be defined as a self-foaming composition for topical application.

A first subject of the present invention is consequently a composition containing trifarotene, intended for leave-on topical application, which is provided in the form of a foam, advantageously of semisolid consistency, which advantageously does not contain any foaming surfactant and which comprises a medium that is pharmaceutically compatible with leave-on topical application, in particular to the skin and integuments.

The term "composition in the form of a foam" (also referred to hereinbelow as a self-foaming composition) means a composition of semisolid consistency having an aerated form comparable to a foam.

The self-foaming composition according to the present invention comprises two intermediate compositions or formulations in variable proportions and in particular the ingredients below:
  at least one intermediate composition or formulation A comprising an agent for activating the gas-generating agent defined below;
  at least one intermediate composition or formulation B comprising a gas-generating agent; and
  trifarotene or one of the pharmaceutically acceptable salts thereof contained in at least one of said intermediate formulations A and B.

According to the invention, the composition is self-foaming, i.e. it foams by simple mixing of the intermediate compositions A and B. A subject of the invention is also the composition in foam form resulting from the mixing of said intermediate compositions A and B.

According to the invention, each intermediate composition (or formulation) may have a viscosity (measured at 25° C. and at atmospheric pressure) of between 1 cP and 500 000 cP, advantageously between 500 cP and 350 000 cP, measured with a conventional method of Brookfield RV DV-II type: spindle 6, speed 2.

According to the invention, the gas generated by the gas-generating agent may be any physiologically compatible gas which allows the production of a foam, for instance carbon dioxide ($CO_2$) or oxygen ($O_2$). Preferably, the gas generated from the gas-generating agent is carbon dioxide ($CO_2$).

According to the invention, since the gas concentration may vary, the amount of bubbles in the composition may vary and may thus give a composition which may range from not very aerated to very strongly aerated.

According to the invention, the term "agent for activating the gas-generating agent" means an ingredient which, by chemical reaction with the gas-generating agent, releases a gas. Preferentially, an acid/base reaction is involved.

Thus, according to the invention, the self-foaming composition may preferentially be in any form ranging from aerated to a highly expanded foam.

The composition according to the invention is suitable for topical application and may also comprise a physiologically acceptable medium, i.e. a medium that is compatible with the skin and integuments. It is preferably a pharmaceutically acceptable medium.

In addition, the composition may comprise any active agent that may have activity, optionally therapeutic activity. These active agents may be chosen, inter alia, from emollients, humectants, free-radical scavengers, anti-inflammatory agents, vitamins, depigmenting agents, antiacne agents, antiseborrheic agents, antifungal agents, keratolytic agents, sunscreens, slimming agents and skin-coloring agents.

According to the invention, the composition in foam form (i.e. ready to be applied) may have a pH of between 2 and 8, preferentially between 4 and 8.

Insofar as the intermediate composition(s) (or formulation(s)) require storage in at least two compartments for reasons of stability of the ingredients, the present invention relates either to a single compartmentalized container (each compartment receiving one intermediate formulation) and preferably comprising two or three compartments, or to a kit comprising each intermediate formulation stored independently from each other and physically separated.

Intimate extemporaneous mixing (directly on the skin or on any other support) of the intermediate formulations makes it possible to obtain the composition in foam form according to the invention.

More specifically, the intermediate composition (or formulation) A may be in the form of a solution, an emulsion (lotion, cream, emulsifier-free cream, milk or fluid cream) or a gel. This composition advantageously contains the agent for activating the gas-generating agent, preferentially an acid, in a sufficient amount (which may be in the form of an acid/base buffer at acidic pH), which may be, as a nonlimiting example, the citric acid/sodium citrate pair. Formulation B may be in the form of a solution, a gel or an emulsion (lotion, cream, emulsifier-free cream, milk or fluid cream). This composition advantageously contains, in a sufficient amount, a gas-generating agent which may in particular be sodium bicarbonate.

Thus, a subject of the invention is also a kit or a single multi-compartment container as defined previously, for the extemporaneous preparation of a composition in foam form according to the invention, separately comprising at least two intermediate formulations (or intermediate compositions):
- an intermediate formulation A comprising at least one agent for activating the gas-generating agent; and
- an intermediate formulation B comprising at least one gas-generating agent;
- trifarotene or one of the pharmaceutically acceptable salts thereof being contained in at least one of said intermediate formulations A and B.

Preferably, trifarotene is contained in the intermediate composition A.

Gas-Activating Agent:

The agent for activating the gas-generating agent (also referred to as the "gas-activating agent") is a compound which reacts with the gas-generating agent via a chemical reaction (preferably an acid/base reaction) which releases a gas.

It is advantageously an acid, a partially salified polyacid salt or a buffer solution of a weak acid and of its conjugate base, or a mixture of such compounds.

According to the invention, the acid/base buffer of said acid may be any acid/base buffer of the weak acid, for instance a citric acid/sodium citrate buffer or a tartaric acid/sodium tartrate buffer. Mention will preferably be made of α-hydroxy acids, which are weak acids preferentially with a pKa of between 2 and 6, such as citric acid, tartaric acid, malic acid or lactic acid, but also phosphoric acid and pyrophosphoric acid and optionally the partially salified salts thereof, such as disodium pyrophosphate or sodium dihydrogen phosphate, also known as monosodium phosphate.

Preferentially, according to the invention, the gas-activating agent is chosen from a tartaric acid/tartrate salt (for example sodium tartrate) buffer; a citric acid/sodium citrate buffer alone; phosphoric acid, monosodium phosphate, disodium pyrophosphate, which are alone or as a mixture with a citric acid/sodium citrate buffer.

According to a very preferred embodiment, the gas-activating agent is a citric acid/sodium citrate buffer, alone or as a mixture with monosodium phosphate and/or disodium pyrophosphate.

In compositions for sensitive skin or for damaged skin, such as acneic skin, the content of citric acid/sodium citrate is preferably less than or equal to 2.4%, relative to the total weight of the intermediate composition A, so as to limit any risk of stinging. In order to improve the tolerance and to avoid the sensation of stinging, preferably, the citric acid/sodium citrate buffer is used as a mixture with disodium pyrophosphate or sodium dihydrogen phosphate.

According to the invention, said gas-activating agent may be present in the intermediate formulation A in an amount that may range from 0.001% to 95% by weight relative to the total weight of the intermediate composition A.

Gas-Generating Agent:

The term "gas-generating agent" means any agent which has the property of generating a gas via a chemical reaction. Mention will be made in this regard of any compound which, when it is mixed with a weak acid, can form a gas via a chemical reaction equivalent to the following:

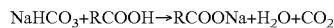

According to the invention, the gas generated from the gas-generating agent present in the intermediate composition B is preferably carbon dioxide ($CO_2$).

According to the invention, the gas-generating agent is preferably chosen from sodium bicarbonate, potassium bicarbonate, sodium carbonate and potassium carbonate, and mixtures thereof.

Preferentially, according to the invention, the intermediate formulation B comprises an agent which generates carbon dioxide, this agent particularly preferably being sodium bicarbonate.

Said gas-generating agent may be present in the intermediate formulation B in an amount ranging from 1% to 10% by weight and preferentially from 2% to 8% by weight, relative to the weight of the intermediate composition B.

According to the invention, the intermediate formulation A may have an acidic pH, advantageously of between 1.0 and 6.0, and the intermediate formulation B may have a basic pH, advantageously of between 7 and 12.

According to the invention, one (or more) intermediate formulation(s) comprise trifarotene, in unmodified form or in salt form, in an amount corresponding to 0.00001% to 20% by weight of trifarotene in acid form (i.e. 3"-tert-butyl-4'-(2-hydroxyethoxy)-4"-pyrrolidin-1-yl[1,1':3',1"]terphenyl-4-carboxylic acid) relative to the total weight of the total composition.

Preferably, the total composition (mixture of the intermediate of formulation A with the intermediate of formulation B) contains trifarotene, in unmodified form or in salt form, in an amount corresponding to 0.00001% to 1% by weight, preferentially from 0.0001% to 0.1% by weight and more preferentially from 0.001% to 0.1% by weight of trifarotene in acid form relative to the weight of the total composition.

In the present description, the term "total composition" or "total formulation" means the composition of the product in foam form after said intermediate compositions have been mixed. Preferably, trifarotene is contained in intermediate composition A which has better compatibility with the active agent.

In fact, the Applicant has discovered that trifarotene could in certain cases have a lesser compatibility with the ingredients constituting the formulation B, and most particularly with sodium bicarbonate.

The intermediate formulation A may be in any galenical form that is compatible with the galenical form desired for the final composition obtained by mixing formulation A with formulation B.

The intermediate formulation B may be in any galenical form that is compatible with the galenical form desired for the final composition obtained by mixing formulation B with formulation A. Advantageously, formulation B may be a gel, a solution, a suspension or an emulsion (cream, surfactant-free cream, lotion, milk or fluid cream), preferably an emulsion.

According to one embodiment of the invention, one of the two intermediate formulations (i.e. intermediate formulation A or intermediate formulation B) is in the form of a gel. In this embodiment, the other intermediate formulation is preferably not in gel form.

Each intermediate formulation of the kit or of the multi-compartment container as defined previously in accordance with the invention comprises a physiologically acceptable medium which conveys the compound(s) and which is chosen such that the compounds are capable of reacting with each other to form a self-foaming composition during the mixing of at least the intermediate formulations A and B.

Thus, the extemporaneous mixing of at least two formulations, for example formulation A and formulation B, creates the composition in foam form according to the invention.

During the mixing of the two formulations A and B, the gas-generating agent, such as sodium bicarbonate, reacts with the gas-activating agent, such as the acid, and thus gives in particular the salt corresponding to the acid, water and $CO_2$ gas. It is this gas, trapped in the bubbles of the composition, which creates the foam which characterizes the self-foaming composition of the invention.

Thus, by mixing at least intermediate formulation A and intermediate formulation B, the foam composition, referred to as the total composition, according to the invention is obtained. Unreacted gas-activating agent and/or gas-generating agent may, of course, remain in the composition obtained after mixing at least formulations A and B.

Advantageously, the kit or the single multi-compartment container according to the invention may be designed so that, during the preparation of the composition according to the invention, the intermediate formulations A and B can be mixed in an A/B weight ratio ranging from 0.5 to 2, preferentially from 0.5 to 1.5, more preferentially close to 1 (i.e. from 0.9 to 1.1) and even more preferentially 1. This means that the kit can be designed to simultaneously release doses (by weight) of the intermediate compositions A and B that may be in a weight ratio ranging from 2 doses of B per 1 dose of A to 2 doses of A per 1 dose of B, preferably from 2 doses of B per 1 dose of A to 3 doses of A per 2 doses of B. According to a preferred embodiment of the invention, the kit is designed to simultaneously release 1 dose by weight of A and 1 dose by weight of B.

According to the invention, the kit may be in any form that is compatible with, on the one hand, separate storage of the intermediate formulations A and B and, on the other hand, the ability to perform extemporaneous mixing of A and B.

For example, the intermediate formulations A and B may be packaged in a case with at least two separate compartments, each containing A or B.

According to another aspect, the kit may be in the form of a syringe having at least two separate bodies, each equipped with a piston, said two bodies containing the respective formulations A and B and being designed to simultaneously release, by exerting a force on the piston, the desired doses of formulations A and B.

The invention also relates to a process for preparing a composition according to the invention, characterized in that, in order to obtain the composition in foam form, an intermediate formulation A and an intermediate formulation B of the kit as are defined above are mixed extemporaneously in relative weight proportions A/B that may range from 0.5 to 2, preferentially from 0.5 to 1.5 and more preferentially 1.

In order to obtain an optimum foam (final composition), the inventors experimentally sought the optimum contents of gas-generating agent (preferably sodium bicarbonate) and of gas-activating agent (preferably citric acid and/or disodium pyrophosphate and/or sodium dihydrogen phosphate or monosodium phosphate).

Thus, it was determined experimentally that when the gas-activating agent is citric acid, the citric acid/sodium bicarbonate weight ratio is advantageously between 0.1 and 2, preferentially between 0.5 and 1 and very preferably equal to 0.7.

Similarly, it was determined experimentally that when the gas-activating agent is disodium pyrophosphate, the disodium pyrophosphate/sodium bicarbonate weight ratio is between 0.5 and 5, preferentially between 1 and 3 and very preferably equal to 2.4.

Similarly, it was determined experimentally that when the gas-activating agent is sodium dihydrogen phosphate, the sodium dihydrogen phosphate monohydrate/sodium bicarbonate weight ratio is between 0.5 and 5, preferentially between 1 and 3 and very preferably equal to 2.

The sodium bicarbonate/citric acid, sodium bicarbonate/sodium pyrophosphate and sodium bicarbonate/sodium hydrogen phosphate ratios are illustrated in example 4.

Surprisingly, the citric acid/sodium citrate, disodium pyrophosphate or sodium dihydrogen phosphate combination and a gelling system that is compatible with the galenical form made it possible to obtain a formulation with very stable physicochemical properties and in which trifarotene is particularly stable, does not generate any unpleasant sensation on the skin and allows the liberation of gas and thus the creation of foam.

Example 2B below shows that the compositions according to the present invention have both excellent physical and chemical stability.

A composition is regarded as being physically stable when its organoleptic characteristics, its pH, its viscosity and the homogeneity of trifarotene do not change over time under various temperature conditions: room temperature (RT) and 40° C.

According to the invention, room temperature corresponds to a temperature ranging from 15° C. to 25° C.

A composition is regarded as being chemically stable when the content of active principle it contains does not change over time under various temperature conditions (RT and 40° C.). According to the invention, the composition is regarded as being stable when the content of trifarotene (expressed by weight relative to the weight of the intermediate formulation) is included in the specifications ranging from 90% to 110%.

The composition according to the invention may also comprise one or more agents chosen from dispersants, stabilizers, preserving agents, fatty substances, thickeners, dyes, fragrances, surfactants, gelling agents, complexing agents, neutralizers, non-foaming emulsifying agents, fillers, sequestrants, reducing agents, odor maskers, plasticizers, softeners, moisturizers, pigments, clays, mineral fillers, mineral colloids, polymers, proteins, nacreous agents, waxes, oils, for instance paraffins or silicones, fatty acids, solid esters of fatty alcohols or of fatty acids, gums and wetting agents.

Water-soluble dyes, such as FD&C Blue 1 (of empirical formula $C_{37}H_{34}N_2Na_2O_9S_3$), and liposoluble dyes such as Sudan Red III or Nile Red, have the advantage of coloring one of the formulation intermediates. This coloring makes it possible to monitor the satisfactory mixing of the two formulation intermediates and to highlight the formation of the foam. This coloring is especially presented in the examples and in FIG. 1.

Gelling Agents for the Intermediate Formulation Comprising the Gas Activator

The intermediate composition A advantageously containing at least one gas-activating agent preferably contains at least one gelling agent and/or suspending agent.

Formulation A may contain large amounts of acid and of electrolytes. The viscosity and the suspending power of these formulations are often difficult to ensure over time.

As nonlimiting examples of gelling agents and/or suspending agents which are resistant simultaneously to electrolytes and to acidic pH values and which may be included in the compositions A according to the invention, mention may be made of ready-to-use mixtures, such as the polyacrylate-13 & polyisobutene & polysorbate 20 mixture sold by SEPPIC under the name Sepiplus 400®, the acrylamide/sodium acryloyldimethyl taurate copolymer & isohexadecane & polysorbate 80 mixture sold by SEPPIC under the name Simulgel 600®, polysaccharides with, as nonlimiting examples, xanthan gum, such as Xantural 180® sold by the company Kelco, gellan gum sold under the name Kelcogel® by the company Kelco, sclerotium gum sold under the name Amigel® by Alban Muller Industrie, guar gum and derivatives thereof, such as the hydroxypropyl guar sold under the name Jaguar HP-105@ by Rhodia, cellulose and derivatives thereof, such as microcrystalline cellulose and sodium carboxymethyl cellulose sold under the name Blanose CMC 7H4XF® by the company Hercules, hydroxypropylmethylcellulose, in particular the product sold under the name Methocel E4M® Premium by the company Dow Chemical, or hydroxyethylcellulose, in particular the product sold under the name Natrosol HHX 250® by the company Aqualon, the family of the magnesium aluminum silicates, such as Veegum K®, Veegum Plus® or Veegum Ultra® sold by the company Vanderbilt, bentonite sold under the name Polargel® HV, the family of modified starches, such as the modified potato starch sold under the name Structure Solanace®, the family of carrageenans, in particular divided into four main families: κ, λ, β and ω, such as the Viscarin® and Gelcarin® products sold by the company IMCD. Alternatively, polyvinyl alcohol, also known under the abbreviation PVA, sold by Merck under the name Polyvinyl Alcohol 40-88®. Preferably, Veegum K® and Xantural 180® will be used in combination.

The gelling agent as described above may be used at preferential concentrations ranging from 0.001% to 15% and more preferentially ranging from 0.15% to 5% by weight relative to the weight of the intermediate formulation A.

Gelling Agents for the Intermediate Formulation Containing the Gas Generator

As nonlimiting examples of gelling agents and/or suspending agents and/or gelling agents that are simultaneously resistant to electrolytes and two basic pH values and which may be included in the intermediate compositions B according to the invention, mention may be made of acrylic acid polymers such as the acrylates/C10-30 alkyl acrylate crosspolymer such as the "electrolyte-insensitive" carbomers sold under the name Ultrez 20®, Ultrez 10®, Carbopol 1382® or Carbopol ETD2020NF®, Aqua SF1® sold by the company Lubrizol, the ammonium acrylate/acrylamide copolymer & polyisobutene & polysorbate 20 mixture sold by SEPPIC under the name Sepiplus 265®, the acrylamide/sodium acryloyldimethyl taurate copolymer & isohexadecane & polysorbate 80 mixture sold by SEPPIC under the name Simulgel 600®, polysaccharides with, as nonlimiting examples, xanthan gum, such as Xantural 180® sold by the company Kelco, gellan gum sold under the name Kelcogel® by the company Kelco, sclerotium gum sold under the name Amigel® by Alban Muller Industrie, guar gum and derivatives thereof, such as the hydroxypropyl guar sold under the name Jaguar HP-105® by Rhodia, cellulose and derivatives thereof, such as microcrystalline cellulose and sodium carboxymethyl cellulose sold under the name Blanose CMC 7H4XF® by the company Hercules, hydroxypropylmethylcellulose, in particular the product sold under the name Methocel E4M® Premium by the company Dow Chemical, or hydroxyethylcellulose, in particular the product sold under the name Natrosol HHX 250® by the company Aqualon, the family of the magnesium aluminum silicates, such as Veegum K®, Veegum Plus® or Veegum Ultra® sold by the company Vanderbilt, bentonite sold under the name Polargel® HV, the family of modified starches, such as the modified potato starch sold under the name Structure Solanace® or the tapioca meal known under the name Naviance Tapioca P® sold by AkzoNobel, or the family of carrageenans, in particular divided into four main families: κ, λ, β and ω, such as the Viscarin® and Gelcarin® products sold by the company IMCD. Preferably, Veegum K® and Xantural 180® will be used in combination.

The gelling agent as described above may be used at preferential concentrations ranging from 0.001% to 15% and more preferentially ranging from 0.15% to 5% by weight relative to the weight of the intermediate formulation B.

Humectants

Among the humectants and/or emollients which may act as skin moisturizer and facilitate the application of the formulation, use is optionally made, without this list being limiting, of compounds such as a polyol that is water-miscible at room temperature (25° C.) chosen especially from polyols especially containing from 2 to 20 carbon atoms, preferably containing from 2 to 10 carbon atoms and preferentially containing from 2 to 6 carbon atoms, such as glycerol, glycol derivatives such as propylene glycol, butylene glycol, pentylene glycol, hexylene glycol, dipropylene glycol, diethylene glycol and mixtures thereof, but also sugars (for example glucose or lactose), polyethylene glycols (PEG) (for example Lutrol E400®), urea, and amino acids (for example serine, citrulline, arginine, asparagine or alanine).

As preferred humectant and/or emollient, mention may be made of glycerol and propylene glycol.

The humectants may be used, alone or in combination, at preferential concentrations ranging from 0.001% to 30% and more preferentially ranging from 0.01% to 10% by weight relative to the weight of the total formulation.

Chelating Agents

Among the chelating agents, mention may be made, as nonlimiting examples, of ethylenediaminetetraacetic acid (EDTA), diethylenetriaminepentaacetic acid (DTPA), ethylenediaminebis(O-hydroxyphenylacetic acid) (EDDHA), hydroxy-2-ethylenediaminetriacetic acid (HEDTA), ethyldiaminebis(O-hydroxy-p-methylphenyl)acetic acid (EDDHMA) and ethylenediaminebis(5-carboxy-2-hydroxyphenyl)acetic acid (EDDCHA).

As preferred chelating agent, mention may be made of ethylenediaminetetraacetic acid (EDTA) sold especially under the name Titriplex III®; it may be used at preferential concentrations ranging from 0.001% to 1% and more preferentially from 0.05% to 0.1% by weight relative to the weight of the total formulation.

Excipients with Complementary Properties

The composition according to the invention may contain one or more cosmetic active agents, for instance, as nonlimiting examples, allantoin with anti-irritant properties, antiacne zinc gluconate, dipotassium glycyrrhizate for its anti-inflammatory properties, or alternatively the cicatrizing agent α-bisabolol or dimethyl isosorbide for its pro-penetrating properties.

Fillers and Particles

Fillers and/or particles may be used to stabilize and boost the foam. Some of them have the specific property of being positioned at the water/air interface and of thus stabilizing this interface. Fillers that may be mentioned include talc, metal oxides such as zinc oxide, titanium dioxide TiO2 T2000 sold by the company Merck under the name Eusolex® T-2000, clays such as laponites, bentones or bentonites, but also cellulose ethers such as Methocel® K100 LV sold by the company Dow, silicas such as Aerosil® R972 sold by the company Evonik or Silice HDK® H13L sold by Wacker; they may be used at concentrations ranging from 0.01% to 10% by weight relative to the weight of the total formulation.

Oils of the Fatty Phase

The composition according to the invention may also comprise a fatty phase. This fatty phase may be present in one and/or the other of the intermediate compositions A and B. Depending on the galenical form of the intermediate formulations, the fatty phase may represent from 0% to 95% by weight relative to the weight of each intermediate formulation.

The fatty phase of the composition according to the invention may comprise, for example, plant, mineral, animal or synthetic oils, silicone oils, and mixtures thereof.

As examples of mineral oils, mention may, for example, be made of liquid paraffins of various viscosities, such as Primol 352®, Marcol 82® and Marcol 152® sold by the company Esso.

As plant oils or derivatives thereof, mention may be made of sweet almond oil such as *Prunus Amygdalus Dulcis* (sweet almond) oil supplied by SICTIA, palm oil, soybean oil, sesame oil, sunflower oil, olive oil and apricot kernel oil and esters thereof such as the product Apricot Kernel Oil PEG-6 Ester (Labrafil M1944CS).

As animal oils or the substitute thereof of plant origin, mention may be made of lanolin, squalene, fish oil with, as a derivative, the perhydrosqualene sold under the name Sophiderm® by the company Sophim.

As synthetic oils, mention may be made of an ester such as cetearyl isononanoate, for instance the product sold under the name Cetiol SN PH® by the company Cognis France, isononyl isononanoate such as Dub ININ® sold by the company Stéarineries Dubois, diisopropyl adipate, for instance the product sold under the name Crodamol DA® by the company Croda, isopropyl palmitate, for instance the product sold under the name Crodamol IPP® by the company Croda, and caprylic/capric triglyceride, such as Miglyol 812® sold by the company Univar. As hydrogenated polyisobutenes, mention may be made of the Parleam® products sold by the company Rossow, PPG-15 stearyl ether (Arlamol PS15 E) supplied by CRODA or PPG-11 stearyl ether (Arlamol PS11E-LQ) supplied by Gattefossé.

As silicone oils, mention may be made of a dimethicone, for instance the product sold under the name Q7-9120 Silicone Fluid® with a viscosity from 20 cSt to 12 500 cSt, by the company Dow Corning, or a cyclomethicone, for instance the product sold under the name ST-Cyclomethicone 5NF®, also by the company Dow Corning.

These oils may be present, alone or in combination, in contents ranging from 0.5% to 50% by weight and preferentially from 2% to 30% by weight relative to the weight of the total composition.

Nonliquid Fatty Substances

The composition according to the invention may also comprise solid fatty substances such as natural or synthetic waxes, fatty acids such as stearic acid, fatty alcohols such as Speziol C18® Pharma or Speziol C16® sold by the company Cognis, and texturing agents of tribehenate type, such as Compritol 888® sold by the company Gattefossé or hydrogenated castor oils such as Cutina HR® sold by the company Cognis or glyceryl stearate such as Geleol® sold by the company Gattefossé or DC 9045 Elastomer Blend® sold by the company Dow Corning.

These nonliquid fatty substances may be used alone or as a mixture from 0% to 30% by weight relative to the weight of the total formulation. However, exceptional foam quality has been observed when fatty alcohols of formula $CH_3(CH_2)_nOH$ (n is between 11 and 23) are present in contents of greater than 1% by weight relative to the weight of the total formulation.

Nonionic Emulsifiers

The composition according to the invention may also comprise one or more nonionic emulsifiers.

Preferred emulsifiers that may be mentioned include hydrophilic emulsifiers such as glyceryl stearate (and) PEG-100 stearate sold under the name Arlacel 165FL® by the company Uniqema, lipophilic emulsifiers such as propylene glycol monocaprylate (Capryol 90) supplied by Gattefossé, propylene glycol laurate (Lauroglycol FCC) supplied by Gattefossé, sorbitan sesquioleate (Arlacel 83VPharma) supplied by Croda, Glucate SS® and Glucamate SSE®, polyoxyethylene (21) stearyl ether sold under the name Brij 721® by the company Uniqema or also in the same family Brij S2® and Brij S20®. The self-emulsifying wax sold by Croda under the name of Polawax NF® or else laureth-4. Mention may also made of nonionic non-foaming emulsifiers with a high HLB, sorbitan esters such as POE(20) sorbitan monooleate sold under the name Tween 80® (HLB=15), POE(20) sorbitan monostearate sold under the name Tween 60® (HLB=14.9), fatty alcohol ethers such as POE (21) stearyl ether (HLB=15.5), or ceteareth-20 sold under the name of Eumulgin B2 PH® by Cognis (HLB of 15.5), or nonionic emulsifiers with a low HLB, sorbitan esters, such as sorbitan monostearate (sold under the name of Span 60® by Uniqema), glycerol esters such as glyceryl monostearate (Cutina GMS® from Cognis), sucrose esters with a low HLB, such as sucrose distearate. In another form according to the invention, the emulsifiers that may be used are polyglycerol esters. They are esters of polyglycerolated fatty acids obtained by condensation of glycerol. Glycolipid emulsifiers, such as Montanov 202® sold by the company SEPPIC. Some emulsifiers may be sold in the form of a mixture, such as Emulium Kappa® and Emulium Delta® sold by Gattefossé. These emulsifiers may be used, alone or as a mixture, so that the HLB of the system is greater than 12 and preferentially greater than 15.

Such emulsifiers may be used at between 0.01% and 30% by weight, relative to the weight of the total composition, preferentially between 0.1% and 15% and more preferentially between 0.5% and 7%.

Preserving Agents:

Examples of preserving agents that may be mentioned include benzalkonium chloride, bronopol, chlorhexidine, chlorocresol and derivatives thereof, ethyl alcohol, phenoxyethanol, potassium sorbate, diazolidinyl urea, benzyl alcohol, parabens and sodium benzoate, or mixtures thereof.

As preferred preserving system, mention may be made of the combination phenoxyethanol and pentylene glycol or sodium benzoate.

The examples that follow illustrate the invention without limiting its scope.

EXAMPLES

Example 1: Formulation Examples

Formulation Examples A: Intermediate Compositions a Containing the Gas-Activating Agent Intermediate formulations A were prepared according to the following process:

Step 1: At a temperature above 60° C., add the gelling agents with stirring to the main water phase.

Step 2: With stirring, introduce trifarotene into an additional phase.

Step 3 (optional): in parallel, melt the fatty phase at a temperature above 60° C. This fatty phase is composed of the emulsifiers, the waxes and the emollient oils.

Step 4 (optional): At a temperature above 60° C., prepare the emulsion by adding the fatty phase to the main phase.

Step 4: Add the additional phase containing trifarotene to the main phase.

Step 5: Cool and add the additives such as the dye, the cosmetic active agents and the humectants.

In the formulation examples below, the amounts are expressed relative to the weight of the intermediate formulation rather than relative to the weight of the total formulation.

Example A1

| INCI name | % by weight |
| --- | --- |
| WATER | QS 100 |
| XANTHAN GUM | 0.5 |
| ACRYLAMIDE, AMPS COPOLYMER DISPERSION 40%/ISOHEXADECANE/POLYSORBATE 80 | 1.5 |
| CETOSTEARYL ALCOHOL | 3 |
| CYCLOPENTASILOXANE | 2 |
| CETEARETH-20 | 3 |
| GLYCERYL DIBEHENATE | 3 |
| PPG-11 STEARYL ETHER | 5 |
| DISODIUM EDTA | 0.1 |
| CITRIC ACID | 1.75 |
| SODIUM CITRATE | 1.3 |
| DISODIUM PYROPHOSPHATE | 6 |
| PHENOXYETHANOL | 1 |
| TRIFAROTENE | 0.02 |

Example A2

| INCI Name | % by weight |
| --- | --- |
| WATER | QS 100 |
| XANTHAN GUM | 0.5 |
| ACRYLAMIDE, AMPS COPOLYMER DISPERSION 40%/ISOHEXADECANE/POLYSORBATE 80 | 1.5 |
| CETOSTEARYL ALCOHOL | 3 |
| CYCLOPENTASILOXANE | 2 |
| CETEARETH-20 | 3 |
| GLYCERYL DIBEHENATE | 3 |
| PPG-11 STEARYL ETHER | 5 |
| DISODIUM EDTA | 0.1 |
| CITRIC ACID | 1.5 |
| SODIUM CITRATE | 0.5 |
| SODIUM DIHYDROGEN PHOSPHATE | 6.2 |
| PHENOXYETHANOL | 1 |
| TRIFAROTENE | 0.02 |

Example A5

| INCI Name | % by weight |
| --- | --- |
| WATER | QS 100 |
| DISODIUM EDTA | 0.1 |
| XANTHAN GUM | 0.7 |
| MAGNESIUM ALUMINUM SILICATE | 2.5 |
| DISODIUM PYROPHOSPHATE | 6 |
| CITRIC ACID | 1.8 |
| SODIUM CITRATE | 1.3 |
| POLOXAMER 124 | 0.2 |
| TRIFAROTENE | 0.02 |
| PROPYLENE GLYCOL | 4.0 |

Example A7

| INCI Name | % by weight |
| --- | --- |
| WATER | QS 100 |
| DISODIUM EDTA | 0.1 |
| XANTHAN GUM | 0.7 |
| MAGNESIUM ALUMINUM SILICATE | 2.5 |
| SODIUM BENZOATE | 0.2 |
| DISODIUM PYROPHOSPHATE | 7.2 |
| CITRIC ACID | 1.4 |
| SODIUM CITRATE | 1 |
| POLOXAMER 124 | 0.2 |
| TRIFAROTENE | 0.02 |
| PROPYLENE GLYCOL | 4.0 |

Formulation Examples B: Intermediate Compositions B Comprising the Gas-Generating Agent The intermediate formulations B were prepared according to the following process:

Step 1': At a temperature above 60° C., add the gelling agents with stirring to the main water phase.

Optional step 2': In parallel, heat the fatty phase (containing the oils, the waxes and the surfactants) to a temperature above 60° C.

Optional step 3': At a temperature above 60° C., prepare the emulsion by adding the fatty phase to the main phase.

Step 4': Add the additives such as the preserving agents or ethanol at a temperature suitable for the additive.

Step 5': Neutralize the mixture.

Step 6': At a temperature below 40° C., add the sodium bicarbonate.

Example B1

| INCI Name | % by weight |
|---|---|
| WATER | QS 100 |
| MAGNESIUM ALUMINUM SILICATE | 2.5 |
| XANTHAN GUM | 0.6 |
| TRIETHANOLAMINE | 1.2 |
| SODIUM HYDROGEN CARBONATE | 5 |
| PHENOXYETHANOL | 0.8 |

Example B2

| INCI Name | % by weight |
|---|---|
| WATER | QS 100 |
| MAGNESIUM ALUMINUM SILICATE | 2.5 |
| XANTHAN GUM | 0.5 |
| CETOSTEARYL ALCOHOL | 3 |
| CETEARETH-20 | 3 |
| GLYCERYL DIBEHENATE | 3 |
| PPG-11 STEARYL ETHER | 5 |
| CYCLOPENTASILOXANE | 2 |
| SODIUM HYDROXIDE | 0.09 |
| SODIUM HYDROGEN CARBONATE | 5 |
| PHENOXYETHANOL | 1 |

Example B3

| INCI Name | % by weight |
|---|---|
| WATER | QS 100 |
| DISODIUM EDTA | 0.1 |
| MAGNESIUM ALUMINUM SILICATE | 2.5 |
| XANTHAN GUM | 0.7 |
| SODIUM HYDROXIDE | 0.09 |
| SODIUM HYDROGEN CARBONATE | 5 |
| PHENOXYETHANOL | 0.8 |

Example B7

| INCI Name | % by weight |
|---|---|
| WATER | QS 100 |
| MAGNESIUM ALUMINUM SILICATE | 2.5 |
| XANTHAN GUM | 0.5 |
| CETEARETH-20 | 3 |
| CETOSTEARYL ALCOHOL | 3 |
| GLYCERYL DIBEHENATE | 3 |
| CAPRYLIC/CAPRIC TRIGLYCERIDE | 6 |
| SODIUM HYDROXIDE | 0.09 |
| PHENOXYETHANOL | 0.8 |
| SODIUM HYDROGEN CARBONATE | 5 |

The mixtures in a 1:1 weight ratio of the intermediate compositions A and B described above are represented in the table below. A cross at the intersection of two formulation intermediates indicates that the mixture was tested and generated a foam having the desired properties.

| | Formulation B | | | |
|---|---|---|---|---|
| Formulation A | B1 | B2 | B3 | B7 |
| A1 | X | X | X | X |
| A2 | X | X | X | X |
| A5 | | X | | X |
| A7 | | X | | X |

Example 2A: Foam Density Measurements

Starting with the formulation examples described in example 1, foam density measurements were taken at the time of placing in contact of the two intermediate formulations A and B (TO) and then when the chemical reaction generated by the placing in contact of the two compositions is complete:

Density placebo formulation A5, i.e. without trifarotene (but with blue colorant)=1.108

Density formulation B7=1.021

Placebo foam A5/B7 (50/50)=0.290

The foam density measurement shows that the volume increased by a factor of 4 and was confirmed by the photographs in FIG. 1. The left-hand photo represents the moment of mixing (TO) and the right-hand photo represents the foam obtained when the acid/base chemical reaction is complete.

Example 2B: Stability

Tables Ia and Ib below collate the physical stability data of the intermediate formulations A1 and A2 described in example 1, containing trifarotene.

| Formulation A1 | T0 | | T1 Month | T3 Months | T6 Months |
|---|---|---|---|---|---|
| Macroscopic appearance | Bright white homogeneous cream | RT | Complies | Complies | Complies |
| | | 40° C. | Complies | Complies | Complies |
| Microscopic observations X400 | Emulsion oil droplets less than 2.5 μm | RT | Complies | Complies | Complies |
| | | 40° C. | Complies | Complies | Complies |
| Brookfield RV DVII Spindle 5, speed 5 Viscosity cP | 27360 | RT | — | — | 23000 |
| | | 40° C. | — | — | 24800 |
| pH | 3.85 | RT | 4.01 | 3.75 | 3.76 |
| | | 40° C. | 3.89 | — | 3.76 |

| Formulation A2 | T0 | | T1 Month | T2 Months | T6 Months |
|---|---|---|---|---|---|
| Macroscopic appearance | Bright white homogeneous cream | RT | Complies | Complies | Complies |
| | | 40° C. | Complies | Complies | Complies |
| Microscopic observations X400 | Emulsion oil droplets less than 5 μm | RT | Complies | Complies | Complies |
| | | 40° C. | Complies | Complies | Complies |
| Viscosity cP Brookfield LV DVII Spindle 66, speed 50 | — | RT | 5902 | 6119 | 6119 |
| | | 5° C. | 5375 | 6287 | — |
| | | 40° C. | 7414 | 6071 | 4900 |
| pH | 3.45 | RT | 3.45 | 3.44 | 3.42 |
| | | 5° C. | 3.47 | 3.56 | — |
| | | 40° C. | 3.46 | 3.45 | 3.48 |

Table II below details the chemical stability data for trifarotene in intermediate formulation A1.

| Formulation A1 | T0 | | T1 Month | T2 Months | T3 Months |
|---|---|---|---|---|---|
| % w/trifarotene (HPLC) | 104.9 | RT | — | 104 | |
| | | 40° C. | 106.3 | 105.7 | 106 |

Example 3: Comparative Study of Measurement of Irritation

Study Protocol.

The study is performed according to the OECD TG 439 protocol in force for the short application time (RHE/product contact time 15 min). This protocol is appropriate for a long application time (RHE/product contact time 18 h).

The objective of this study is to evaluate the tolerance of the supports of the complete and intermediate formulations on reconstructed human epidermides (RHE, Episkin model) through:
 evaluation of the reduction of MTT (cell viability)
 measurement of the release of IL-1alpha (irritation marker)

The formulations tested are:
An intermediate a composition of acidic formulation: placebo example A7 (i.e. not containing trifarotene),
An intermediate composition of basic formulation: example B7,
The complete formulation composed of the mixture: A7 placebo+B7 (in a 50/50 weight ratio),
A commercial reference in cream form.

Study Results:

| Mixture tested | Short exposure Viability (%) | Long exposure Viability (%) | Conclusion Irritant potential |
|---|---|---|---|
| B7 | 89.8 | 93.3 | Non-irritant |
| A7 placebo | 86.0 | 84.5 | Non-irritant |
| Complete formulation | 95.8 | 83.4 | Non-irritant |
| Commercial ref. | 99.8 | 91.1 | Non-irritant |

| Mixture tested | Short exposure IL-1a vs control | Long exposure IL-1a vs control |
|---|---|---|
| B7 | 1.5 | 2.0 |
| A7 placebo | 2.2 | 2.3 |
| Complete formulation | 1.9 | 3.1 |
| Commercial ref. | 2.4 | 3.6 |

The MTT measurements according to the OECD protocol in force indicate that all the formulations tested are non-irritant.

The assay of IL-1a of the complete formulation according to the invention after a short exposure time and a long exposure time shows a lower content of irritation markers than after application of the commercial reference.

Example 4

The ideal content of citric acid, sodium pyrophosphate and sodium dihydrogen phosphate monohydrate to react with 5% of sodium bicarbonate was established empirically. The values are expressed as weight/weight percentages relative to the weight of each of the two intermediate formulations.

|                                         | Ratio 1 | Ratio 2 | Ratio 3 |
|-----------------------------------------|---------|---------|---------|
| Sodium bicarbonate                      | 5%      | 5%      | 5%      |
| Citric acid                             | 3.5%    | —       | —       |
| Disodium pyrophosphate                  | —       | 12      | —       |
| Sodium dihydrogen phosphate monohydrate | —       | —       | 7.2%    |

In order for the pH of the formulation containing the gas activator to have optimum compatibility with the skin, sodium citrate was added so as to create a citric acid/sodium citrate buffer.

Part of the citric acid/sodium citrate buffer may advantageously be replaced with disodium pyrophosphate and vice versa like the contents cited by way of example in the table below:

Table III: the values are expressed as weight/weight percentages relative to the weight of each of the two intermediate formulations.

|                        | E 1  | E2   | E 3  | E 4 | E 5  | E 6   | E 7  |
|------------------------|------|------|------|-----|------|-------|------|
| Sodium bicarbonate     | 5%   | 5%   | 5%   | 5%  | 3%   | 3%    | 3%   |
| Citric acid            | 3.5% | 1.75%| 1.4% | 0   | 2.1% | 1.05% | 0    |
| Sodium citrate         | 2.7% | 1.3% | 1%   | 0   | 1.6% | 1.15% | 0    |
| Disodium pyrophosphate | 0    | 6%   | 7.2% | 12% | 0    | 3.6%  | 7.2% |

Part of the citric acid/sodium citrate buffer may advantageously be replaced with sodium dihydrogen phosphate monohydrate and vice versa, like the contents cited by way of example in table IV below:

Table IV: the values are expressed as weight/weight percentages relative to the weight of each of the two intermediate formulations.

|                                         | E1   | E8   | E9  |
|-----------------------------------------|------|------|-----|
| Sodium bicarbonate                      | 5%   | 5%   | 5%  |
| Citric acid                             | 3.5% | 1.5% | 0   |
| Sodium citrate                          | 2.7% | 0.5% | 0   |
| Sodium dihydrogen phosphate monohydrate | 0    | 6.2% | 10% |

In one particular embodiment, it was determined that when the amount of citric acid is greater than or equal to 1.4, the amount of foam is optimal when disodium pyrophosphate is present in the composition according to the following equation:

$$[C] = 2.4[B] - 2.4[A]/0.7$$

when:
[C]=weight content of disodium pyrophosphate in the intermediate composition A
[A]=weight content of citric acid monohydrate in the intermediate composition A
[B]=weight content of sodium bicarbonate in the intermediate composition B The above equation thus makes it possible to calculate the optimum contents between sodium bicarbonate, citric acid and sodium pyrophosphate.

Example 5: Comparative Study of Release Profile-Permeation

The aim of this study is to evaluate the penetration and distribution of various formulations according to the invention in human skin.

Study Protocol:

The formulations tested in this study are applied to excised whole human skin samples mounted on a Franz cell at a rate of 5 mg/cm$^2$ at 32° C.

After 16 hours of application, trifarotene is assayed in: the fraction not absorbed, the stratum corneum, the epidermis, the dermis and the receiver fluid.

This study makes it possible to study the influence of the formulation on the release of the active principle and its permeation through the skin. The object is to compare the distribution of trifarotene in the various skin layers in the case of the application of a well-known formulation and the application of a composition in chemical foam form.

The formulations tested are:
Reference in cream form containing 0.01% trifarotene, and
A complete chemical foam formulation containing 0.01% trifarotene, composed of the mixture: A2+B3 (in a 50/50 weight ratio).

Diffusion Cells:

The diffusion cells used are static diffusion cells, on the basis of the Franz model diffusion cell, with the following characteristics:
Application area=2 cm$^2$
Volume of the receiver fluid compartment=3 ml The receiver compartment is surrounded by a water jacket heated at 37° C.±1° C. to ensure a temperature of 32° C.±1° C. at the skin surface. The receiver compartment is separated from the donor compartment by the skin membrane, the epidermal face being on the donor side. The receiver compartment containing a magnetic stirring bar was filled with the receiver fluid so as to prevent any formation of air bubbles. During the diffusion time, the receiver fluid was stirred continuously so as to ensure homogenization.

Preparation of the Skin Samples:

Abdominal skin samples derived from cosmetic surgery were used in this study. On arrival of the samples, the hypodermis was separated from the assembly using tweezers, and the remaining material was washed gently and stored flat in aluminum foil for storage at −20° C. On the day of the experiment, the skin samples were thawed and then cut into pieces to be compatible with the geometry of the diffusion cell.

The skin samples, derived from donors 42, 44 and 69 years old, were mounted on the diffusion cell with PBS as receiver fluid. The mean skin thickness was 0.89±0.07 mm with a maximum of 1.39 mm and a minimum of 0.45 mm. Thicknesses of all the specimens.

After at least 45 minutes at equilibrium with the receiver fluid, the skin integrity was evaluated by measuring the trans-epidermal water loss (TEWL). All the cells whose TEWL measurements were outside the acceptance criteria are carefully cleaned and left at equilibrium for a prolonged period before remeasuring the TEWL. The mean TEWL value was 5.51±1.63 g/m$^2$/h.

Study Parameters:
Room temperature: 21.7° C.
Relative humidity 45.6%

Study Results:

In the stratum corneum, there were no significant differences in cutaneous penetration between the formulations (foam according to the invention and cream), as illustrated in FIG. 2.

In the epidermis, the penetration the chemical foam formulations differs very little from the cream reference (according to example A2+B3 as a 50:50 mixture), as illustrated in FIG. 2.

In the dermis, the chemical foam compositions penetrate less than the cream reference (according to example A2+B3 as a 50:50 mixture), as illustrated in FIG. 3.

None of the receiver fluid samples was quantifiable, irrespective of the test formulation; this suggests low systemic exposure.

The present study confirms the obtaining of a foam which remains on the surface of the skin, so as to avoid the undesirable effects such as irritation and to obtain a foam which is suitable for the treatment of acne.

The invention claimed is:

1. A self-foaming leave-on topical composition comprising:
   (a) at least one intermediate composition B comprising a gas-generating agent, wherein the gas-generating agent is selected from the group consisting of sodium bicarbonate, potassium bicarbonate, sodium carbonate, and potassium carbonate, and mixtures thereof;
   (b) at least one intermediate composition A comprising an agent for activating the gas-generating agent, wherein the agent for activating the gas-generating agent is a citric acid/sodium citrate buffer, alone or as a mixture with sodium phosphate and/or disodium pyrophosphate; and
   (c) 0.01% to 0.1% by weight, relative to the weight of the total composition, of trifarotene or a pharmaceutically acceptable salt thereof present in intermediate composition(s) A and/or B;
   wherein the self-foaming leave-on composition does not comprise any lipophilic emulsifiers.

2. The composition as claimed in claim 1, wherein the trifarotene is present in the intermediate composition A.

3. The composition as claimed in claim 1, wherein the composition does not comprise any foaming surfactants selected from the group consisting of anionic surfactants, cationic surfactants, amphoteric surfactants, and nonionic surfactants of the family of alkylpolyglucosides and glucamides.

4. The composition as claimed in claim 1, wherein the gas generated from the gas-generating agent is carbon dioxide.

5. The composition as claimed in claim 1, wherein the gas-generating agent is present in the intermediate composition B in an amount ranging from 1% to 10% by weight, relative to the weight of the intermediate composition B.

6. The composition as claimed in claim 1, wherein the intermediate composition B has a pH of between 7 and 12.

7. The composition as claimed in claim 1, wherein the agent for activating the gas-generating agent is present in the intermediate composition A in an amount ranging from 0.001% to 95% by weight relative to the weight of the intermediate composition A.

8. The composition as claimed in claim 1, wherein the intermediate composition A has an acidic pH.

9. The composition as claimed in claim 1, wherein the intermediate composition A is in the form of a solution, a gel, or an emulsion.

10. The composition as claimed in claim 1, wherein the intermediate composition B is in the form of a solution, a gel, or an emulsion.

11. The composition as claimed in claim 1, wherein the composition is formulated for use in the treatment of acne.

12. The composition as claimed in claim 3, wherein the composition does not comprise any foaming surfactants.

13. The composition as claimed in claim 1, wherein the gas-generating agent is sodium bicarbonate.

14. The composition as claimed in claim 5, wherein the gas-generating agent is present in the intermediate composition B in an amount ranging from 2% to 8% by weight.

15. The composition as claimed in claim 6, wherein the pH is basic.

16. The composition as claimed in claim 8, wherein the acidic pH is from 1.0 to 6.0.

17. The composition as claimed in claim 9, wherein the intermediate composition A is in the form of a gel.

18. The composition as claimed in claim 10, wherein the intermediate composition B is in the form of an emulsion.

19. A cosmetic method comprising topically administering an effective amount of the self-foaming leave-on topical composition as claimed in claim 1, to the skin of an individual subject in need thereof.

20. A kit or single multi-compartment container containing a self-foaming leave-on topical composition, the composition comprising:
   (a) at least one intermediate composition B comprising at least one gas-generating agent, wherein the gas-generating agent is selected from the group consisting of sodium bicarbonate, potassium bicarbonate, sodium carbonate, and potassium carbonate, and mixtures thereof;
   (b) at least one intermediate composition A comprising at least one agent for activating the gas-generating agent, wherein the agent for activating the gas-generating agent is a citric acid/sodium citrate buffer, alone or as a mixture with sodium phosphate and/or disodium pyrophosphate; and
   (c) 0.01% to 0.1% by weight, relative to the weight of the total composition, of trifarotene or a pharmaceutically acceptable salt thereof present in intermediate composition(s) A and/or B;
   wherein intermediate compositions A and B are separately contained and generate gas upon mixing; and
   wherein the self-foaming leave-on topical composition does not comprise any lipophilic emulsifiers.

21. The kit or container as claimed in claim 20, wherein the kit or container is designed for mixing the intermediate compositions A and B in an A/B weight ratio ranging from 0.5 to 2.

22. The kit or container as claimed in claim 21, wherein the A/B weight ratio ranges from 0.5 to 1.5.

23. The kit or container as claimed in claim 21, wherein the A/B weight ratio ranges from 0.9 to 1.1.

24. The kit or container as claimed in claim 21, wherein the A/B weight ratio is 1.

25. A process for preparing a self-foaming leave-on topical composition in foam form, the process comprising mixing:
   (a) at least one intermediate composition B comprising at least one gas-generating agent, wherein the gas-generating agent is selected from the group consisting of sodium bicarbonate, potassium bicarbonate, sodium carbonate, and potassium carbonate, and mixtures thereof; and
   (b) at least one intermediate composition A comprising at least one agent for activating the gas-generating agent, wherein the agent for activating the gas-generating agent is a citric acid/sodium citrate buffer, alone or as a mixture with sodium phosphate and/or disodium pyrophosphate;
   wherein trifarotene or a pharmaceutically acceptable salt thereof is present in intermediate composition A and/or B at a concentration of 0.01% to 0.1% by weight, relative to the weight of the total composition; and wherein the self-foaming leave-on topical composition does not comprise any lipophilic emulsifiers.

26. The process as claimed in claim 25, wherein the A/B weight proportion ranges from 0.5 to 1.5.

27. The process as claimed in claim 25, wherein the A/B weight proportion is 1.

28. A method for treating acne, comprising applying to the skin of a human subject in need thereof a self-foaming composition obtained by mixing at least two intermediate compositions, the intermediate compositions comprising:
(a) at least one intermediate composition B comprising at least one gas-generating agent, wherein the gas-generating agent is selected from the group consisting of sodium bicarbonate, potassium bicarbonate, sodium carbonate, and potassium carbonate, and mixtures thereof;
(b) at least one intermediate composition A comprising at least one agent for activating the gas-generating agent, wherein the agent for activating the gas-generating agent is a citric acid/sodium citrate buffer, alone or as a mixture with sodium phosphate and/or disodium pyrophosphate; and
(c) 0.01% to 0.1% by weight, relative to the weight of the total composition, of trifarotene or a pharmaceutically acceptable salt thereof present in intermediate composition(s) A and/or B;
wherein the self-foaming composition does not comprise any lipophilic emulsifiers.

* * * * *